United States Patent [19]
Lenker et al.

[11] Patent Number: 5,824,041
[45] Date of Patent: Oct. 20, 1998

[54] APPARATUS AND METHODS FOR PLACEMENT AND REPOSITIONING OF INTRALUMINAL PROSTHESES

[75] Inventors: Jay A. Lenker, Los Altos; Kirsten Freislinger, Menlo Park; Michael A. Evans, Palo Alto; Gwendolyn A. Watanabe, Mountain View; Timothy J. Ryan, Los Gatos; Christopher K. Zarins, Portola Valley; Richard O. Murphy, Mountain View, all of Calif.

[73] Assignee: Medtronic, Inc., Minneapolis, Minn.

[21] Appl. No.: 683,806

[22] Filed: Jun. 28, 1996

Related U.S. Application Data

[63] Continuation of Ser. No. 388,561, Feb. 13, 1995, abandoned, which is a continuation-in-part of Ser. No. 339,911, Nov. 14, 1994, abandoned, which is a continuation-in-part of Ser. No. 290,021, Aug. 12, 1994, abandoned, which is a continuation-in-part of Ser. No. 255,681, Jun. 8, 1994, abandoned.

[51] Int. Cl.⁶ .................................................. A61F 2/06
[52] U.S. Cl. .............................................. 623/1; 606/195
[58] Field of Search ....................... 623/1, 12; 606/194, 606/195

[56] References Cited

U.S. PATENT DOCUMENTS

| | | | |
|---|---|---|---|
| 4,140,126 | 2/1979 | Choudhury | 128/325 |
| 4,562,596 | 1/1986 | Kornberg | 623/1 |
| 4,577,631 | 3/1986 | Kreamer | 128/334 |
| 4,617,932 | 10/1986 | Kornberg | 128/334 |
| 4,787,899 | 11/1988 | Lazarus | 623/1 |
| 4,793,348 | 12/1988 | Palmaz | 128/325 |
| 4,820,298 | 4/1989 | Leveen et al. | 623/1 |
| 4,886,062 | 12/1989 | Wiktor | 128/343 |
| 4,913,141 | 4/1990 | Hillstead | 606/108 |
| 4,950,227 | 8/1990 | Savin et al. | 604/8 |
| 4,969,890 | 11/1990 | Sugita et al. | 606/192 |

(List continued on next page.)

FOREIGN PATENT DOCUMENTS

| | | |
|---|---|---|
| 0 274 846 A1 | 7/1988 | European Pat. Off. . |
| 0 364 420 A1 | 4/1990 | European Pat. Off. . |
| 0 364 420 B1 | 4/1990 | European Pat. Off. . |
| 0 461 791 A1 | 12/1991 | European Pat. Off. . |
| 0 466 518 A3 | 1/1992 | European Pat. Off. . |
| 0 506 686 A1 | 9/1992 | European Pat. Off. . |
| 0 508 473 A2 | 10/1992 | European Pat. Off. . |
| 0 518 704 A1 | 12/1992 | European Pat. Off. . |
| 0 518 839 A2 | 12/1992 | European Pat. Off. . |
| 0 533 511 A1 | 3/1993 | European Pat. Off. . |
| 0 536 610 A1 | 4/1993 | European Pat. Off. . |
| 0 539 237 A1 | 4/1993 | European Pat. Off. . |
| 0 575 719 A1 | 12/1993 | European Pat. Off. . |
| 0 596 145 A1 | 5/1994 | European Pat. Off. . |
| 0 657 147 A2 | 6/1995 | European Pat. Off. . |
| 260 819 | 1/1970 | U.S.S.R. . |
| WO 93/17636 | 9/1993 | WIPO . |
| WO 95/29725 | 11/1995 | WIPO . |
| WO 96/13228 | 5/1996 | WIPO . |
| WO 96/18361 | 6/1996 | WIPO . |
| WO 96/22122 | 7/1996 | WIPO . |
| WO 97/03624 | 2/1997 | WIPO . |

OTHER PUBLICATIONS

Hawley's Condensed Chemical Dictionary, 12th ed., (1993), p. 531.

*Primary Examiner*—Michael J. Milano
*Attorney, Agent, or Firm*—Townsend and Townsend and Crew LLP

[57] ABSTRACT

A delivery catheter for a radially compressible tubular prosthesis comprises an elongate shaft slidably received within an elongate sheath. The prosthesis is carried over the distal end of the shaft where it is contained in a radially compressed configuration by the sheath. After introducing the catheter to a desired target location within a body lumen, the prosthesis may be released by proximally retracting the sheath. The prosthesis will remain anchored to the shaft during at least part of the release procedure, permitting the user to recapture the prosthesis by distally advancing the sheath.

14 Claims, 15 Drawing Sheets

U.S. PATENT DOCUMENTS

| | | | |
|---|---|---|---|
| 4,990,151 | 2/1991 | Wallsten | 606/108 |
| 5,019,085 | 5/1991 | Hillstead | 606/108 |
| 5,035,706 | 7/1991 | Gianturco et al. | 606/198 |
| 5,037,427 | 8/1991 | Harada et al. | 606/108 |
| 5,078,720 | 1/1992 | Burton et al. | 606/108 |
| 5,078,726 | 1/1992 | Kreamer | 606/194 |
| 5,089,005 | 2/1992 | Harada | 606/194 |
| 5,092,877 | 3/1992 | Pinchuk | 623/1 |
| 5,098,440 | 3/1992 | Hillstead | 606/108 |
| 5,104,399 | 4/1992 | Lazarus | 623/1 |
| 5,147,370 | 9/1992 | McNamara et al. | 606/108 |
| 5,158,548 | 10/1992 | Lau et al. | 604/96 |
| 5,190,058 | 3/1993 | Jones et al. | 128/898 |
| 5,192,297 | 3/1993 | Hull | 606/195 |
| 5,201,757 | 4/1993 | Heyn et al. | 606/198 |
| 5,211,658 | 5/1993 | Clouse | 623/1 |
| 5,219,355 | 6/1993 | Parodi et al. | 606/191 |
| 5,242,399 | 9/1993 | Lau et al. | 604/104 |
| 5,272,971 | 12/1993 | Fredericks | 101/136 |
| 5,275,622 | 1/1994 | Lazarus et al. | 623/1 |
| 5,282,824 | 2/1994 | Gianturco | 606/198 |
| 5,306,294 | 4/1994 | Winston | 606/195 |
| 5,433,723 | 7/1995 | Lindenberg et al. | 606/198 |
| 5,478,349 | 12/1995 | Nicholas | 606/198 |
| 5,480,423 | 1/1996 | Ravenscroft et al. | 623/1 |
| 5,507,768 | 4/1996 | Lau et al. | 606/198 |
| 5,562,724 | 10/1996 | Vorwerk et al. | 623/1 |
| 5,562,726 | 10/1996 | Chuter | 623/1 |
| 5,693,083 | 12/1997 | Baker | 623/1 |

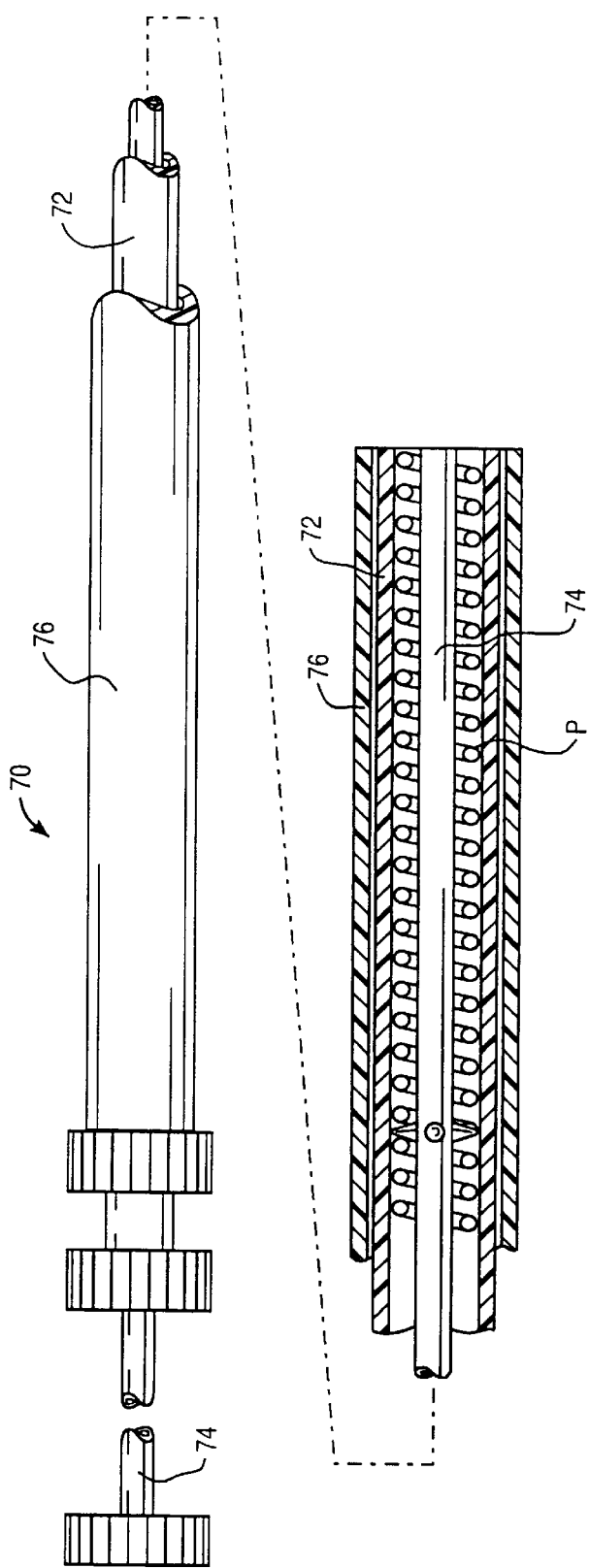
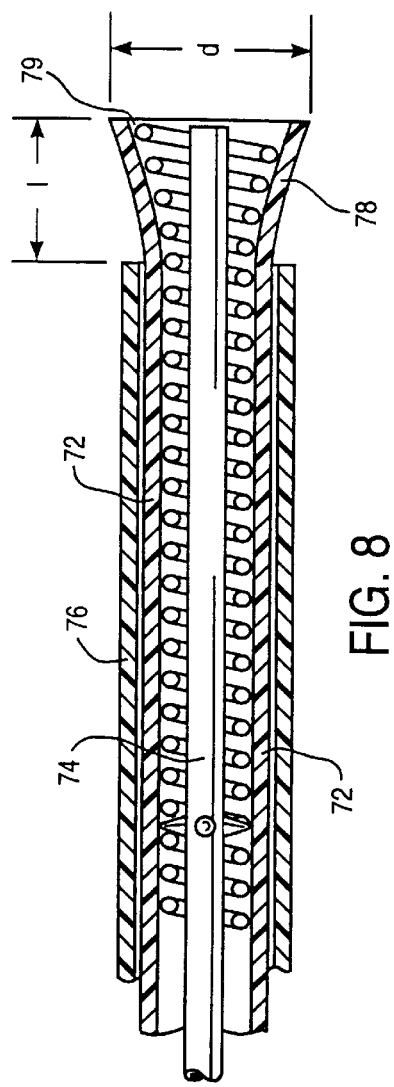
FIG. 7
FIG. 8

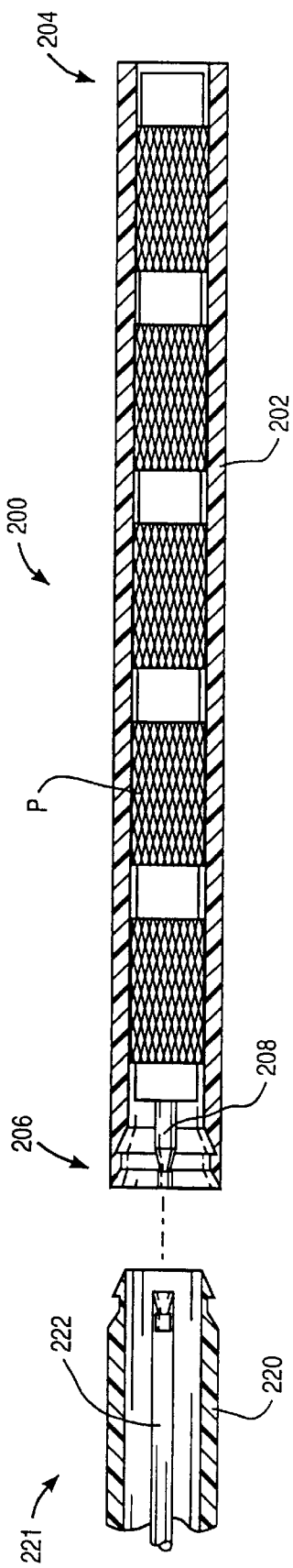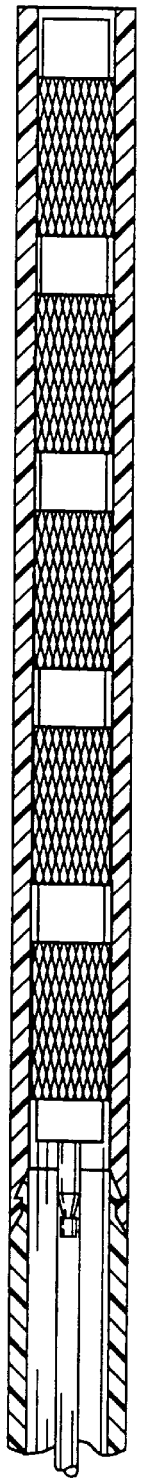
FIG. 17
FIG. 18

APPARATUS AND METHODS FOR PLACEMENT AND REPOSITIONING OF INTRALUMINAL PROSTHESES

This application is a continuation of application Ser. No. 08/388,561, filed on Feb. 13, 1993, now abandoned, continuation-in-part of application Ser. No. 08/339,911, filed Nov. 14, 1994, now abandoned, which was a continuation-in-part of application Ser. No. 08/290,021, filed on Aug. 12, 1994, now abandoned, which was a continuation-in-part of application Ser. No. 08/255,681, filed on Jun. 8, 1994, now abandoned, the full disclosures of which are incorporated herein by reference.

BACKGROUND OF THE INVENTION

1. Field of Invention

The present invention relates generally to apparatus and methods for the endoluminal placement of tubular prostheses, such as grafts, stents, and other structures. More particularly, the present invention relates to a delivery catheter for the initial placing and optional repositioning of such intraluminal tubular protheses in body lumens such as blood vessels for the treatment of abdominal and other aneurysms.

Vascular aneurysms are the result of abnormal dilation of a blood vessel, usually resulting from disease and/or genetic predisposition which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate, usually from 3% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular graft placement for the treatment of aneurysms has been proposed. Although very promising, many of the proposed methods and apparatus suffer from other problems. In particular, delivery and placement of the endovascular graft within the vasculature can be problematic. Proper positioning and sizing of the endovascular graft is critical to the successful treatment of an aneurysm. With many endovascular graft structures and their associated delivery catheters, however, it is difficult or impossible to retract a partially released graft structure. Thus, improper initial placement of a vascular graft can sometimes require open surgical procedures for correction. Additionally, proper sizing of the graft can require maintenance of a large inventory of graft delivery catheters, where each catheter carries a graft having a different length and/or expansible diameter.

For these reasons, it would be desirable to provide improved apparatus and methods for endovascular placement of intraluminal protheses, including both grafts and stents, for treating aneurysms and other conditions. It would be particularly desirable to provide delivery catheters and methods for the placement of endoluminal and other tubular prostheses which permit the repositioning and/or retrieval of partially released prostheses. It would be further desirable if such delivery catheters were able to contain the protheses firmly within the catheter until the final release of the prostheses into the blood vessel.

2. Description of the Background Art

Vascular grafts and devices for their endoluminal placement are described in U.S. Pat. Nos. 5,282,824; 5,272,971; 5,242,399; 5,219,355; 5,211,658; 5,201,757; 5,192,297; 5,190,058; 5,158,548; 5,147,370; 5,104,399; 5,092,877; 5,078,726; 5,019,085; 4,990,151; 4,950,227; 4,913,141; 4,886,062; 4,820,298; 4,787,899; 4,617,932; 4,562,596; 4,577,631; and 4,140,126; and European Patent Publications 539,237; 533,511; 518,839; 518,704; 508 473; 505,686; 466 518; and 461 791. Catheters for placing vascular stents are described in U.S. Pat. Nos. 5,192,297; 5,092,877; 5,089, 005; 5,037,427; 4,969,890; and 4,886,062. Catheters carding a graft structure in a tube or capsule are described in U.S. Pat. Nos. 5,275,622; 5,104,399; and 4,787,899; and EP466518.

SUMMARY OF THE INVENTION

The present invention provides apparatus and methods for the endoluminal placement of intraluminal prostheses, including both grafts and stents, for the treatment of disease conditions, particularly aneurysms. The intraluminal prostheses will comprise a radially compressible, tubular frame having a proximal end, a distal end, and an axial lumen between said ends. In the case of graft prostheses, an inner liner, typically a fabric, polymeric sheet, membrane, or the like, will line all or most of the surface of the lumen of the tubular frame, usually extending from a near-proximal location to a near-distal location. Suitable graft structures for placement using the catheters and methods of the present invention are described in copending application Ser. No. 08/255,681, the full disclosure of which is incorporated herein by reference.

The intraluminal prostheses of the present invention are suitable for a wide variety of therapeutic uses, including stenting of the ureter, urethra, biliary tract, and the like. The devices and methods will also be useful for the creation of temporary or long term lumens, such as the formation of fistulas. The present invention will find its greatest use, however, in the placement of endovascular grafts into blood vessels for the treatment of abdominal and other aneurysms, vascular stenoses, and the like.

According to the present invention, a delivery catheter for positioning a radially compressible tubular prosthesis comprises an elongate flexible shaft having a proximal end and a distal end. A retaining structure is disposed near the distal end of the shaft and releasably holds the prosthesis to maintain the axial position of the prosthesis on the shaft. A sheath is slidably received over the shaft and radially compresses the prothesis while the prosthesis remains axially held by the retaining structure. Alternatively, the retaining structure can comprise a separate cover structure which maintains radial compression of the prostheses as the sheath is proximally retracted.

The prosthesis can be partially released from the catheter into a blood vessel or other body lumen by axially retracting the sheath to allow the prosthesis to expand and conform to the interior surface of the lumen being treated. The prosthesis, however, will remain attached to the catheter shaft by the retaining structure, and so long as the prosthesis remains attached, it can be recaptured simply by distally advancing the sheath back over the expanded portion of the prosthesis to radially compress it back on to the underlying shaft. In this way, the prosthesis can be recaptured and optionally repositioned and rereleased. Alternatively, the prosthesis can be withdrawn from the body lumen entirely.

In order to facilitate release and optional recapture of the prosthesis relative to the catheter, the sheath is preferably provided with a flared distal end. In a first particularly preferred design, a mechanism will be provided for reconfiguring the distal end of the sheath between a non-flared configuration (maintained during introduction of the catheter to a target location in the body lumen) and a flared configuration. For example, an inflatable bladder may be provided at the distal end, where inflation of the bladder causes the distal end of the sheath to flare radially outward. Alternatively, the distal end may include a resilient structure having a fixed, outwardly flared configuration. During introduction of the catheter to the body lumen, the resilient flared end may be radially confined, e.g., by a slidable containment sleeve disposed over the sheath or by an axially translatable cap structure which can capture the flared end of the sheath. As yet another alternative, the distal structure of the sheath may comprise heat memory alloy components which remained non-flared at low temperatures (to facilitate introduction) but which assume the desired flared structure when introduced to a body temperature environment.

As an alternative or in addition to the flared distal end of the prosthesis-containment sheath, the catheter may be provided with a tubular membrane which is attached at one end to the shaft at a location proximal of the retaining structure and at the other end to the inside of the sheath. The membrane is thus disposed to envelope the prosthesis once a prosthesis is received in its radially compressed configuration within the sheath. As the sheath is proximally retracted, a radially outward portion of the tubular member is drawn backwards, causing the tubular member to evert to release the expanding prosthesis while continuing to cover the portion of the prosthesis which is being released from the sheath. By providing a tubular membrane formed from a lubricous material, release and optional recapture of the radially compressible prosthesis can be greatly facilitated.

The retaining structure on the catheter shaft which anchors the prosthesis can take a variety of forms. Most simply, the retaining structure can comprise a plurality of locking stays which extend radially outward to penetrate the prosthesis and engage the interior wall of the sheath. Such locking stays are preferably circumferentially spaced-apart over the region of the catheter shaft which is axially aligned near the proximal end of the prosthesis when held on the shaft. In this way, the prosthesis will be held in place as the containment sheath is proximally translated in order to release the prosthesis. As a particular advantage, the prosthesis will also be held firmly in place if it is desired to distally advance the sheath in order to recapture the partially expanded prosthesis.

In an alternative configuration, the retaining structure comprises a pair of axially-spaced-apart locking stays and a pull wire which passes through each of the locking stays. By further passing the pull wire through the radially compressible prosthesis, the prosthesis may be held in place on the catheter shaft until the pull wire is removed. A wide variety of other specific mechanisms for retaining the prosthesis on the catheter shaft are also available.

The retaining structure may also comprise a cover which is detachably secured over the radially compressible prosthesis where the delivery catheter further includes a mechanism operable from the proximal end of the flexible shaft for detaching the cover to release the prothesis. Usually, the covered prosthesis will be further contained within the axially slidable sheath so that the sheath is first retracted to expose the cover, and the cover is then released from the radially expansible prosthesis within the blood vessel or other body lumen.

The detachable cover may comprise a variety of structures and/or mechanisms but will usually be a cylindrical structure encased around the prosthesis. Exemplary covers and detachment mechanisms include a cord which may be drawn proximally in order to split the cylinder along at least one axial or spiral line. Alternatively, the cover can comprise a plurality of resilient, radially flared axial elements which are held in place by an axially translatable end cap. The end cap may be selectively distally advanced in order to release the axial elements from around the prosthesis. As further a alternative, the cover may be axially weakened along a circumferential or helical line, where a proximal portion of the cover may be drawn in a proximal direction in order to separate the cover into two halves which release the prosthesis from therebetween.

In yet another aspect of the delivery catheter of the present invention, a journal sleeve may be slidably disposed over the prosthesis-containing sheath in order to permit external anchoring of the catheter while the sheath remains free to axially translate relative to the journal sleeve and shaft. Preferably, a lock will be provided to selectively attach the shaft to the journal sleeve while permitting the sheath to be axially translated. In this way, the position of the catheter shaft and radially compressed prosthesis (which is held thereon) may be fixed within the body lumen and then locked into place by locking the journal sleeve within an introducer sheath or other access device which is provided for percutaneous access. After the shaft and prothesis are locked in place, the sheath may be proximally retracted in order to release the prosthesis (allowing it to radially expand) without disturbing the preset position of the prosthesis within the lumen.

In yet another preferred aspect of the catheter introducing system of the present invention, a prosthesis cartridge for use with a delivery catheter comprises (1) a shaft extension having a proximal end, a distal end, and a coupling member at the proximal end, and (2) a sheath extension having a proximal end, a distal end, and a coupling member at the proximal end. A prosthesis is radially compressed over the shaft extension and within the sheath extension. The prosthesis cartridge can be connected to a delivery catheter including an elongate flexible shaft having a proximal end, a distal end, and a coupling member at the distal end for mating with the coupling member on the shaft extension. The delivery catheter will further include an elongate member slidably attached to the shaft and having a proximal end, a distal end, and a coupling member at the distal end for mating with the coupling member on the sheath extension. By providing prosthesis cartridges having a variety of useful lengths and/or diameters, the need for maintaining a large inventory of delivery catheters can be greatly reduced. Moreover, having an available inventory of precompressed prostheses, such as vascular grafts or stents, which are maintained sterilely greatly facilitates use of the delivery catheter system.

According to the method of the present invention, a shaft having a radially compressed prosthesis on its distal end is positioned at a target location within a body lumen, such as a blood vessel. A sheath which is disposed over the prosthesis to maintain its radial compression is then retracted in a proximal direction to permit radial expansion of the prosthesis while the prosthesis remains axially anchored on the shaft. Optionally, the sheath may be distally advanced to recompress and recapture the prosthesis at any time while the prosthesis remains anchored to the shaft. After the sheath has been substantially entirely retracted over the prosthesis, the prosthesis is released from the shaft to effect implantation. Preferably, both the shaft sheath are percutaneously introduced to the body lumen.

In a preferred aspect, the method of the present invention further comprises flaring a distal end of the sheath to facilitate retraction and optional advancement of the sheath over the prosthesis. The sheath may be flared by any of the mechanisms described above in connection with the apparatus of the present invention. Alternatively, the method can further comprise everting a tubular membrane which covers the prosthesis within the sheath as the sheath is proximally retracted. The membrane prevents direct contact between the sheath and the prosthesis and thus facilitates release and recapture.

BRIEF DESCRIPTION OF THE DRAWINGS

FIGS. 7 and 8 illustrate a second embodiment of the delivery catheter of the present invention, wherein a prosthesis-containing sheath has a flared distal end which is open and closed by a sliding sleeve.

FIG. 17 and 18 illustrate a prosthesis cartridge constructed in accordance with the principles of the present invention.

DESCRIPTION OF THE PREFERRED EMBODIMENT

The present invention provides apparatus and methods for the endoluminal placement of intraluminal tubular prostheses, particularly grafts and stents. The tubular prostheses will be radially compressible, and the apparatus of the present invention will maintain the prostheses under compression in a narrow-diameter configuration while they are being introduced to the body lumen typically during a percutaneous introduction procedure. Placement of the tubular prosthesis is effected by releasing the prosthesis at a target location in the lumen. Thus, it is necessary that the prosthesis be sufficiently elastic to expand against the interior wall of the body lumen. It will be appreciated, however, that the prosthesis may be formed at least partly from malleable components which permit it to be subsequently further expanded, typically by inflation of a balloon within the lumen of the prosthesis.

Figure 1:
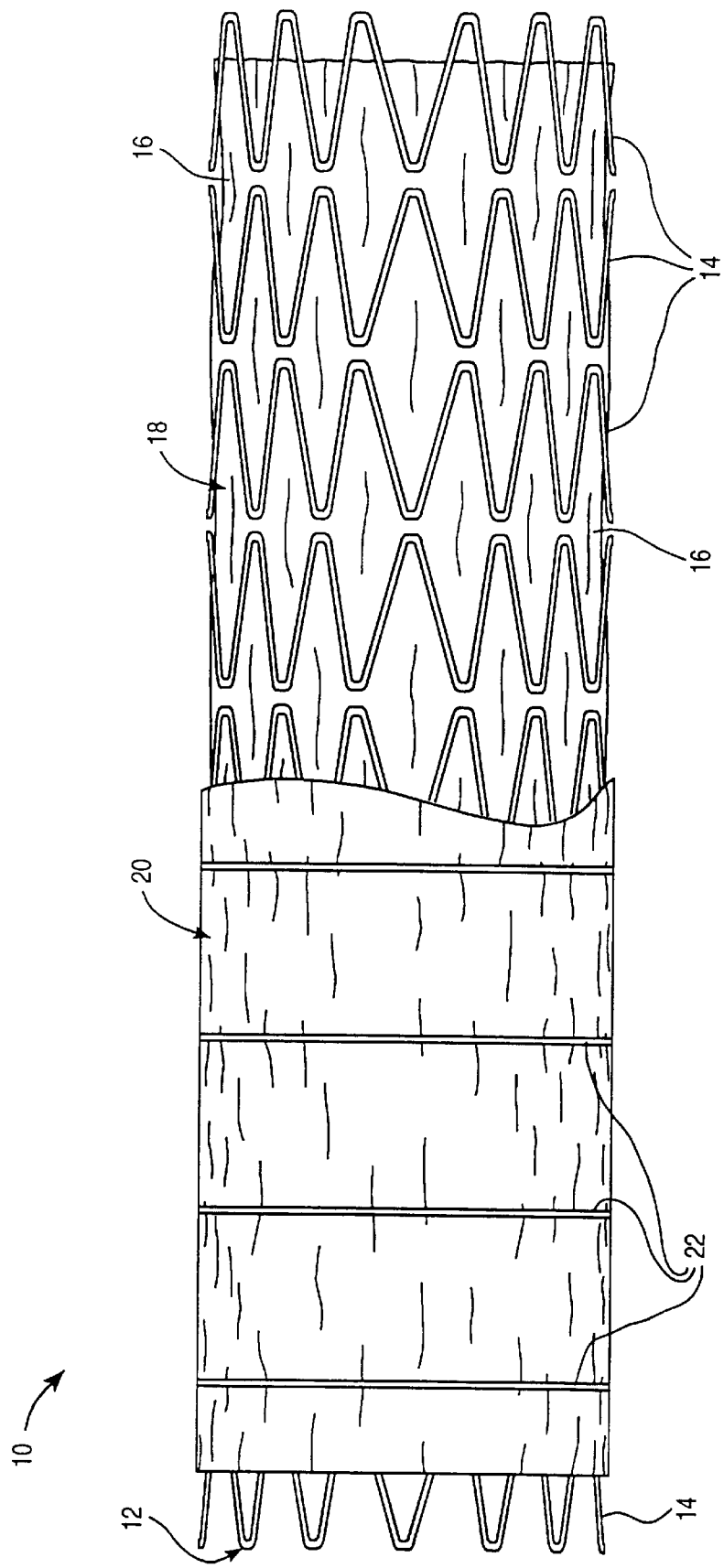
FIG. 1 is a side view of a vascular graft which is exemplary of the type of radially compressible tubular prosthesis which may be placed and optionally recaptured using the delivery catheter of the present invention.

The present invention will find greatest use in the percutaneous placement of endovascular grafts and stents for the treatment of diseases of the vasculature, particularly aneurysms, stenoses, and the like. Suitable graft structures which may be deployed by the delivery catheter of the present invention are described in copending application Ser. No. 08/255,681, the full disclosure of which is incorporated herein by reference. One exemplary graft structure 10 is illustrated in FIG. 1. Graft 10 comprises a perforate tubular frame 12 which includes a plurality of independent (non-connected) band members 14 separated from each other by small gaps 16. The tubular frame 12 is covered by an inner liner 18 and an outer liner 20, where the inner and outer liners together encase or sandwich the otherwise free-floating band members 14 therebetween. In order to secure the band members 14 in place, and secure the liners to the perforate tubular frame 12, the inner and outer liners are joined together along circumferential lines 22, preferably aligned with the gaps 16 between adjacent band members 14. The liners may be joined together by stitching, heat welding, ultrasonic welding, or the like. In the exemplary embodiment, the liners 18 and 20 are formed from polymeric sheet material and are joined together by ultrasonic welding. The band members 14 at each end of the graft 10 will have to be further secured to the liners 18 and 20. For example, they could be stitched, welded, or otherwise joined to the liners to hold them in place. The graft 10 will typically have a length in the range from about 50 mm to 500 mm, preferably from 80 mm to 200 mm, with a relaxed diameter in the range from about 4 mm to 45 mm, preferably being in the range from 5 mm to 25 mm. Such graft structures will be particularly suitable for treating vascular aneurysms.

Figure 2:
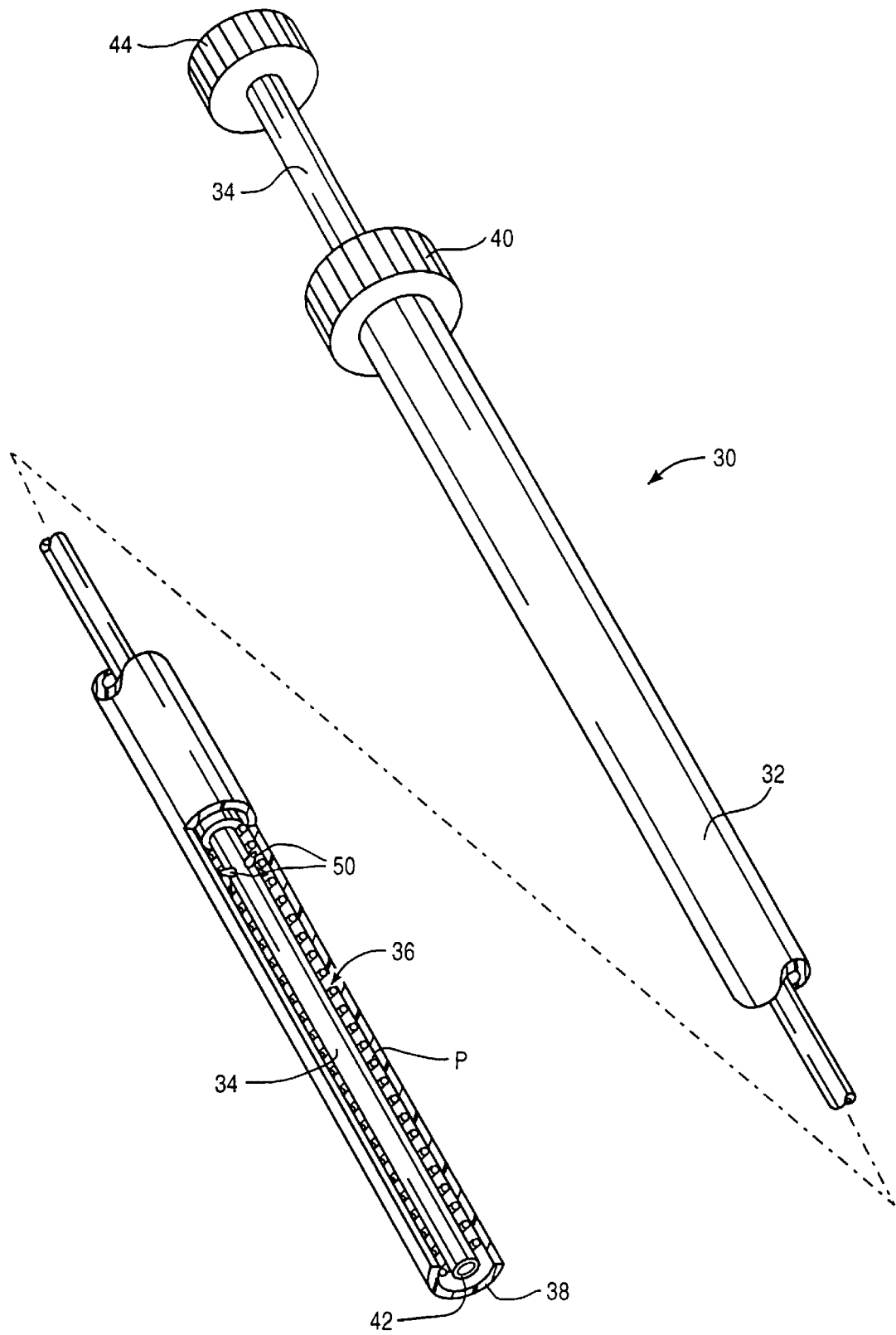
FIG. 2 is a perspective view of a first embodiment of a delivery catheter of the present invention.

Referring now to FIG. 2, a delivery catheter 30 constructed in accordance with the principles of the present invention comprises a sheath 32 and a shaft or inner catheter body 34. The sheath 32 has a central lumen 36 extending from a distal end 38 to a proximal handle 40. The shaft 34 is slidably received within the central lumen 36 and has a distal end 42 and a proximal handle 44. The delivery catheter 30 receives a radially compressible tubular prosthesis P within the annular space between the outer surface of the shaft 34 and the inner surface of the lumen through sheath 32. For convenience, the prosthesis is illustrated as a radially compressed helical coil which expands by unwinding and axial shortening. The delivery catheters of the present invention, however, can be used with virtually any radially compressible prosthesis, as described above.

The delivery catheter of FIG. 2 relies on maintaining the radial compression of prosthesis P by direct pressure from the sheath 32. As will be discussed in detail below in connection with FIGS. 19–24, prosthesis compression may also be provided by a retaining structure which comprises a cover, spaced-apart anchors, or other equivalent structure which maintains the radial compression regardless of the position of the sheath. Using such embodiments, the prosthesis may be uncovered and located prior to release and radial expansion.

Figure 4:
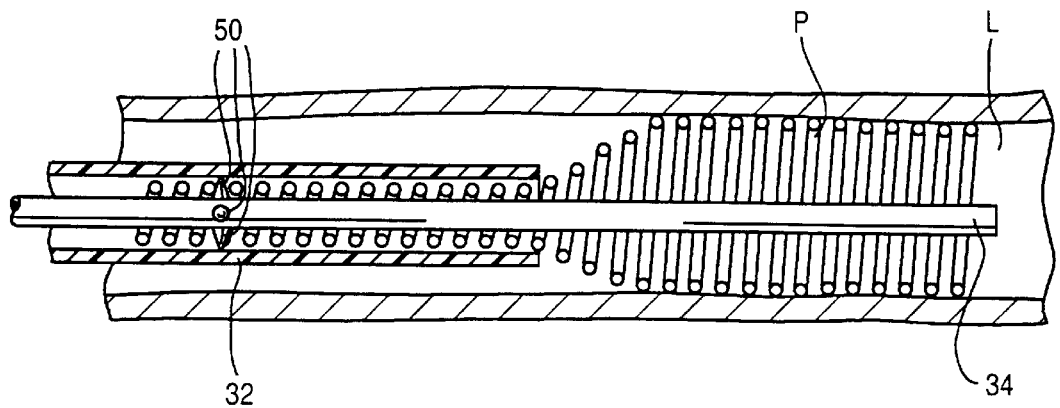
Figure 5:
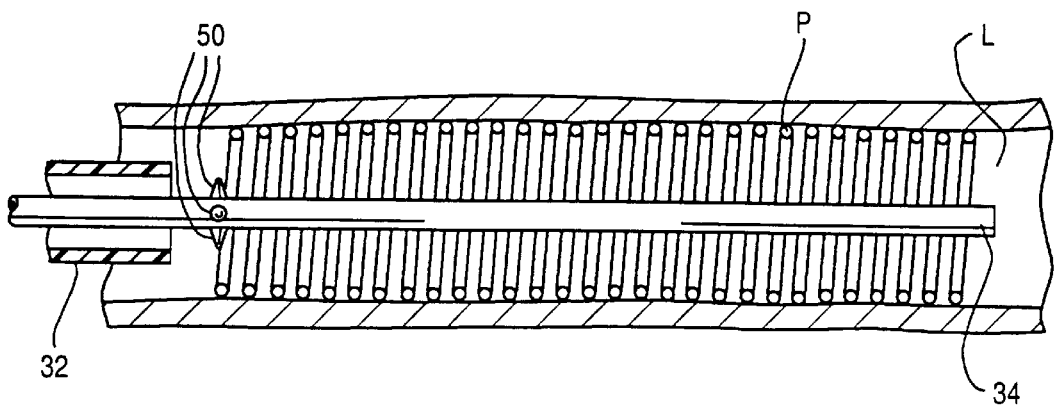

In the embodiment of FIG. 2, the prosthesis P is anchored by a plurality of penetrating stay members 50 which are circumferentially spaced-apart over the exterior of the shaft 34. The stays 50 will be spaced proximally from the distal end 42 of the shaft 34 by a distance which corresponds generally to that of the tubular prosthesis P which is to be maintained on the delivery catheter 30. The penetrating stays 50 will extend radially outward by a distance sufficient to engage the interior surface of the lumen 36 of the sheath 32. In that way, the penetrating stays 50 will be able to anchor the proximal end of the tubular prothesis P when it is held within the catheter. In particular, the prosthesis P will remain anchored as the sheath 32 is drawn proximally over the shaft 34, as illustrated in FIGS. 3–5.

Figure 3:
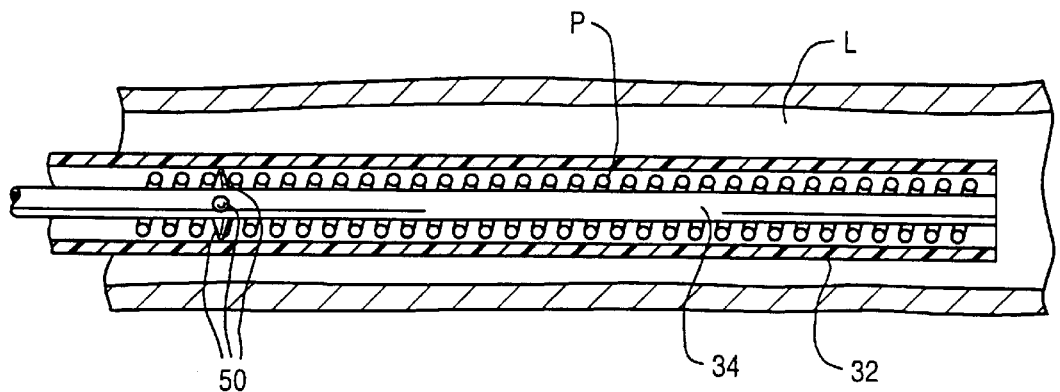
FIGS. 3–5 illustrate the use of the delivery catheter of FIG. 2 in placement of a radially compressible tubular prosthesis in a body lumen.

When initially placed in a body lumen L, the sheath 32 covers substantially the entire length of the prosthesis P with the penetrating stays 50 engaging the proximal portion of the prosthesis P, as illustrated in FIG. 3. The sheath 32 may then be retracted proximally, partially releasing the prosthesis P, as illustrated in FIG. 4. The proximal portion of the prosthesis P, however, remains anchored by the penetrating stays 50 so long as the sheath 32 remains positioned over the stays. Once the sheath 32 is withdrawn to the proximal side of the stays 50, as illustrated in FIG. 5, the prosthesis P will be fully released. Prior to such full release, however, the prosthesis P may be recaptured by advancing the sheath 32 in the distal direction relative to the shaft 32.

Figure 6:
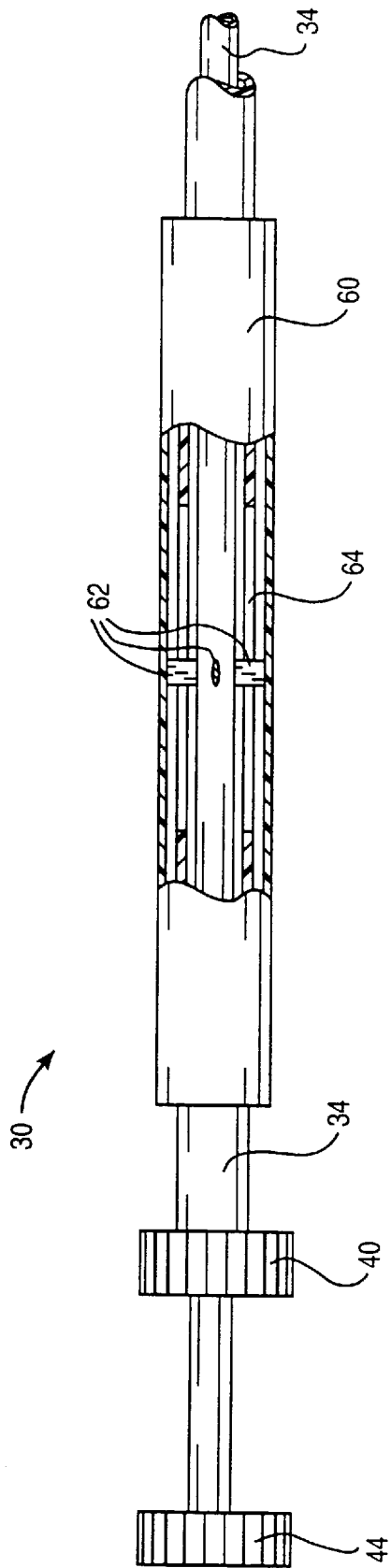
FIG. 6 illustrates placement of a journal sleeve at the proximal end of the delivery catheter of FIG. 2.

Referring now to FIG. 6, the catheter 30 may optionally be provided with a journal sleeve 60 near its proximal end. The journal sleeve 60 is preferably mechanically coupled to the shaft 34 by pins 62 which extend through slots 64 in the sheath 32. The journal sleeve 60 can be anchored within an introducer sleeve or other access device (not illustrated) which is used to provide percutaneous access to the body lumen being treated. After initial positioning of the catheter 30 so that the prosthesis P is located at the target location within the lumen, it is desirable to firmly anchor the catheter 30 within the introducer sheath. Journal sleeve 60 permits anchoring of the shaft 34 (which carries the prosthesis P) while allowing the sheath 34 to remain freely translatable relative to both the journal sleeve 60 and the catheter shaft 34.

The dimensions and materials of construction of the catheter 30 may vary widely, depending on the intended usage. For vascular applications, the catheter 30 will typically have a length in the range from about 50 cm to 250 cm, preferably from 100 cm to 200 cm, and a diameter in the length from about 3 mm to 8 mm, preferably from 4 mm to 6 mm. These dimensions generally refer to the exterior dimensions of the sheath 32. It will be appreciated that the catheter shaft 34 will have a smaller diameter, typically in the range from 1 mm to 5 mm, preferably from about 1.5 mm to 3 mm, allowing a sufficient annular space therebetween to receive the prosthesis P. The catheter shaft will also have a length which is greater than that of the sheath, usually by a distance sufficient to accommodate the length of the prosthesis which is being delivered, typically from 5 cm to 25 cm, preferably from 7.5 cm to 15 cm. The catheters will generally be constructed of natural or synthetic polymers, such as silicone rubber, natural rubber, polyvinylchloride, polyurethanes, polyesters, polyethylenes, polytetrafluoroethylenes (PTFE), and the like. Optionally, the catheter sheath and shaft may be formed as composites having a reinforcement layer incorporated within a polymeric body in order to enhance strength, flexibility, and toughness. Suitable reinforcement layers include wire mesh layers, braided layers, and the like. The tubular members of the present invention may be formed by extrusion, with the tubular diameter modified by heat expansion and/or shrinkage using conventional techniques. Particular techniques for forming vascular and other catheters suitable for use in the present invention are well described in the patent and medical literature.

Referring now to FIGS. 7 and 8, a catheter 70 having a sheath 72 with a deployable flared end will be described. Catheter 70 comprises the sheath 72, a shaft 74, and a prosthesis-containment sheath 76. A prosthesis P is contained between the sheath 72 and the shaft 74, generally as described above in connection with delivery catheter 30. The sheath 72, however, differs from that of sheath 32 in that sheath 72 has an outwardly flared distal end 78, as best seen in FIG. 8. The distal end 78 is a resilient structure, typically formed from the material of the sheath 72 itself and optionally having a plurality of elastic reinforcement elements imbedded therein to maintain the desired flared configuration, and may be radially collapsed by the containment sleeve 76, as illustrated in FIG. 7. The flared distal end of the sheath 72 is advantageous since it facilitates the release and recapture of the prosthesis P.

The flared distal end 78 of catheter 70 will usually have a fully expanded diameter d at the distal tip 79 in the range from 10 mm to 30 mm, preferably from 15 mm to 25 mm. The distal tip of diameter d will usually be greater than the diameter of the proximal portions of the sheath 72 by a factor from 2 to 8, preferably being from 2.5 to 5. The flare will extend over an axial length l in the range from 3 mm to 30 mm, preferably from 5 mm to 20 mm. These flare dimensions will generally be applicable to all embodiments of the present invention where the prosthesis-containment sheath has a flared distal end.

Figure 9:
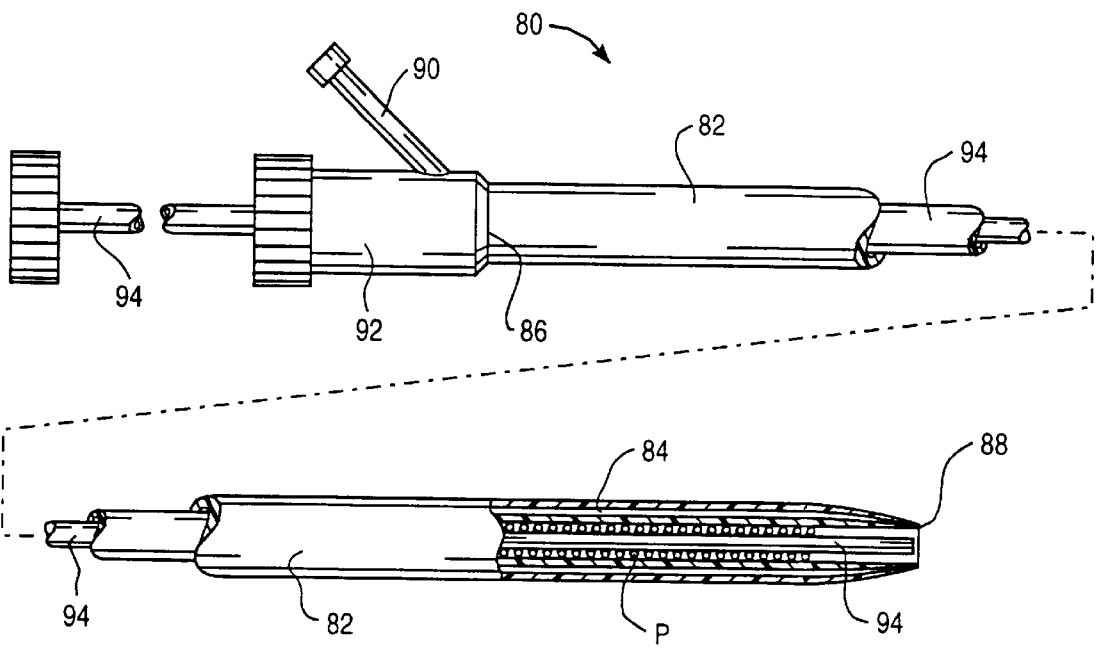
FIGS. 9 and 10 illustrate a third embodiment of the delivery catheter of the present invention wherein the prosthesis-containing sheath has a distal end which may be flared by inflating a bladder surrounding its distal end.
Figure 10:
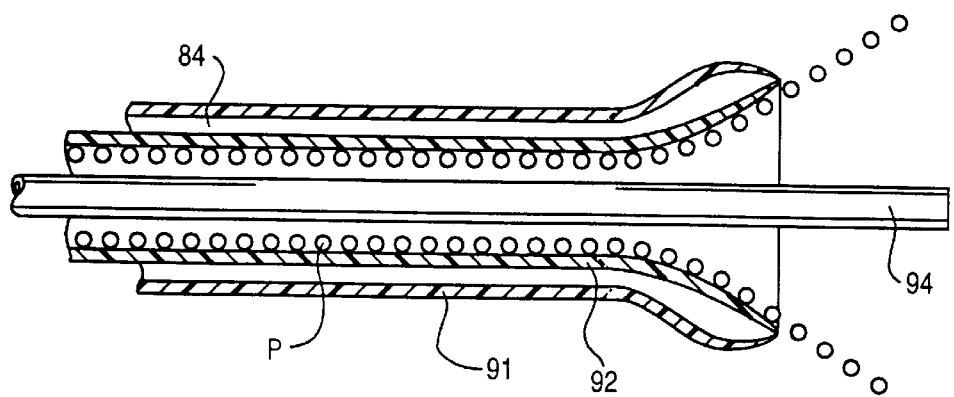

Referring now to FIGS. 9 and 10, a catheter 80 having an alternate mechanism for deploying a flared distal tip on a prosthesis-containing sheath structure 82 will be described. Catheter 80 comprises the sheath 82 having an annular lumen 84 extending from its proximal end 86 to its distal end 88. The annular lumen 84 is connected to an inflation port 90 on a proximal housing 92. A shaft 94 extends through the central lumen of the sheath 82 and carries a prosthesis P near it distal end.

The distal end of the sheath 82 is formed so that, upon inflation with a non-compressible fluid medium, typically saline or other biocompatible liquid, it assumes the outwardly flared configuration shown in FIG. 10. The structure is sufficiently elastic, however, so that removal of the inflation medium will permit the sheath 82 to resume its non-flared configuration, as illustrated in FIG. 9. Flaring of the distal end of sheath 82 facilitates both release and recapture of the prosthesis P, as with the embodiment of FIGS. 7 and 8.

Conveniently, distal end 88 of sheath structure 82 comprises an outer layer 91 secured to an inner layer 92 at their respective distal ends. Both layers 91 and 92 will be composed of a flexible, non-distendable material, such as polyethylene terephthalate (PET), or other reinforced material, such as an elastomeric or non-elastomeric material reinforced with a non-distendable mesh. The outer layer will be shorter than the inner layer so that when the annular lumen 84 is inflated, the distal end will flare as shown in FIG. 10.

Figure 11:
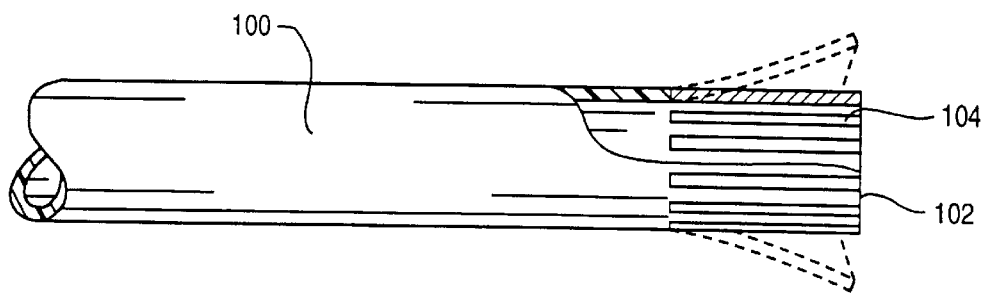
FIG. 11 illustrates a delivery catheter sheath having a flared end including heat memory alloy components.
Figure 12:
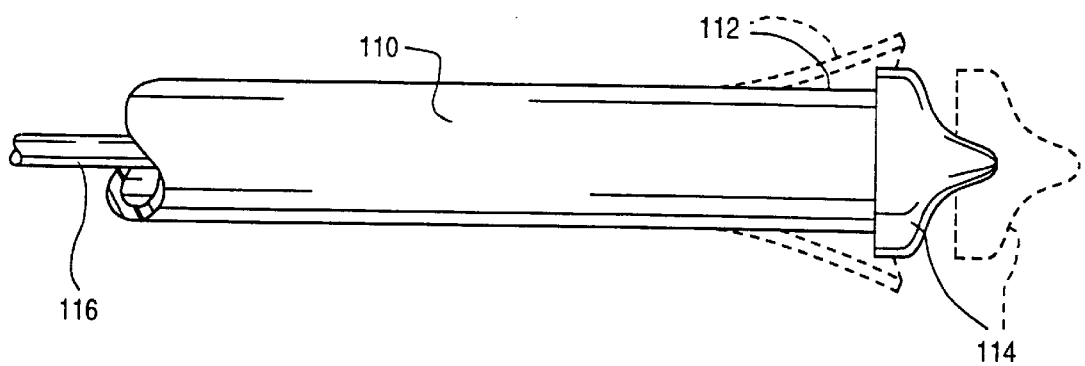
FIG. 12 illustrates a delivery catheter sheath having a flared distal end which is contained within an axially translatable cap.

Alternative mechanisms for providing a deployable flare at the distal end of a prosthesis-containment sheath are illustrated in FIGS. 11 and 12. The sheath 100 in FIG. 11 has a distal end 102 including a plurality of axially aligned, circumferentially spaced-apart heat memory alloy members 104. The heat memory alloys are selected to have a temperature transition where they assume a straight, non-flared configuration at low temperatures, as illustrated in full line in FIG. 11. At body temperature, however, the members 104 assume an outwardly flared configuration, as illustrated in. broken line. Suitable alloy materials include nickel-titanium alloys which may be heat treated to provide the proper shapes and transition temperature.

Sheath 110 illustrated in FIG. 12 has a resilient, flared structure formed at its distal end 112. The flared distal end 112 is contained in an end cap 114 which may be distally advanced (as illustrated in broken line) by shaft 116 to release the flared end structure, as shown in broken line.

Figure 13:
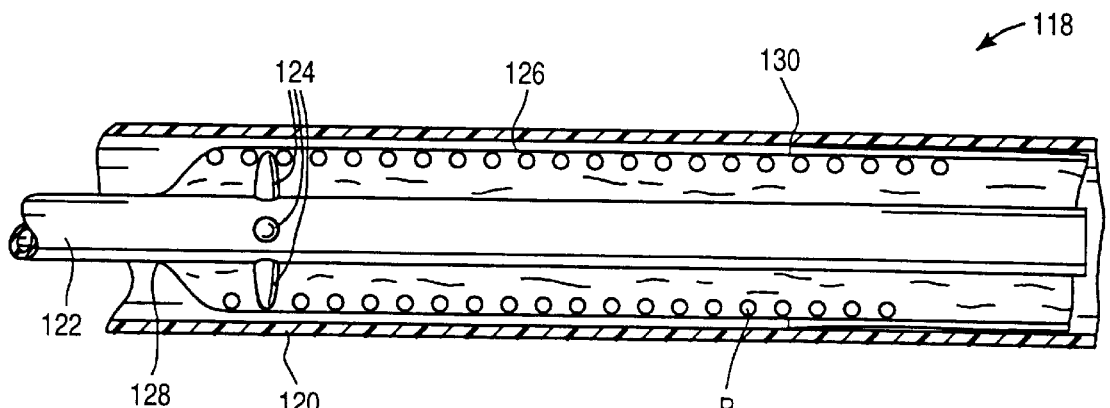
FIG. 13–15 illustrate a fourth embodiment of the delivery catheter of the present invention having an eversible membrane for containing a radially compressible prosthesis.
Figure 14:
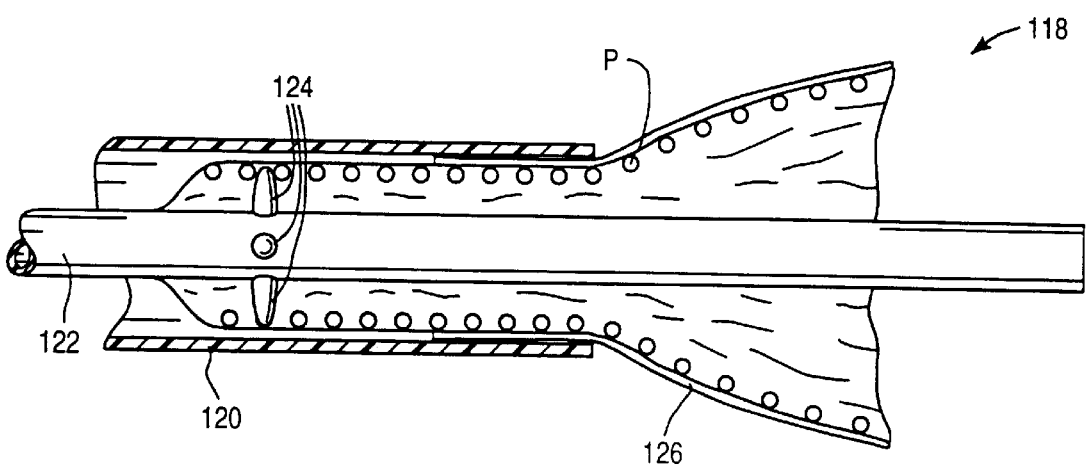
Figure 15:
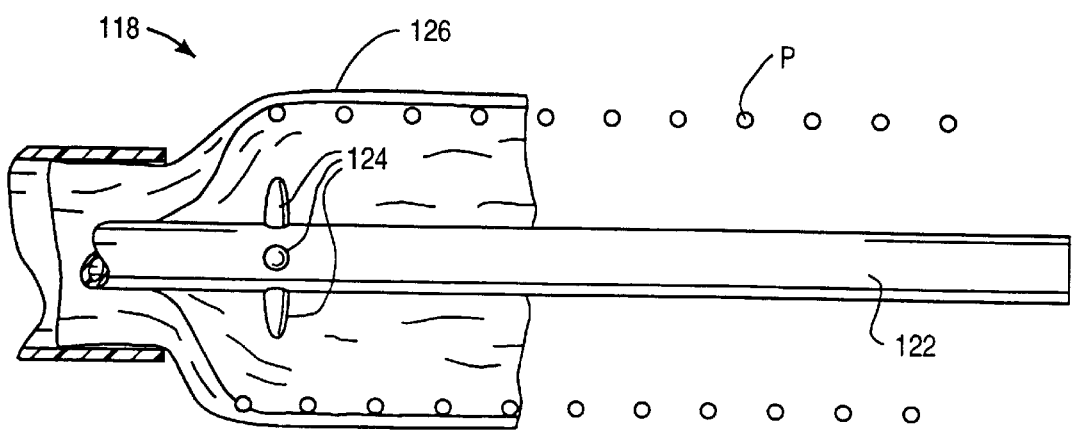

An alternative structure for facilitating the release and recapture of a prosthesis from a delivery catheter according to the present invention is illustrated in FIGS. 13–15. A catheter 118 is provided with a sheath 120, shaft 122, and penetrating stays 124, generally as described above in connection with FIGS. 2–5.

The catheter 118 further includes an eversible membrane 126 which is attached at a first end 128 to the shaft 122, and at a second end 130 to the inner surface of the lumen of sheath 120. The membrane 126 will be formed from a flexible, preferably lubricous and non-compliant material, such as PET, nylon, polytetrafluoroethylene (PTFE), any of which may be wire- or braid-reinforced, or the like. The prosthesis P will remain anchored on the shaft 122 by penetrating stays 124 as the sheath 120 is partially withdrawn (FIG. 14). The membrane 126 folds back over itself (everts) as the sheath 120 is retracted so that there are always two layers of the membrane between the distal end of the sheath and the prosthesis P. The double-layer structure of the membrane provides a high degree of lubricity during the release and optional recapture of the prosthesis P. Complete release of the prosthesis P is illustrated in FIG. 15.

Figure 16:
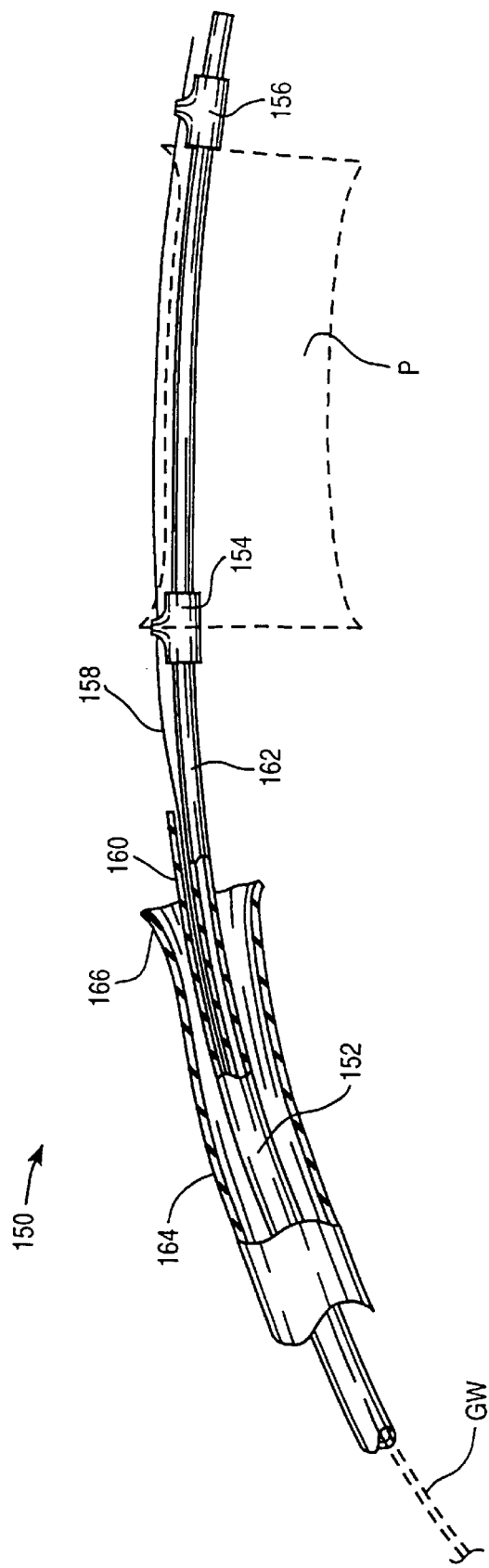
FIG. 16 illustrates a delivery catheter wherein a prosthesis is anchored to the catheter shaft by a pull wire.

Referring now to FIG. 16, an alternative prosthesis anchoring mechanism for a delivery catheter 150 is illustrated. The delivery catheter 150 includes a shaft 152 having a pair of axially spaced-apart stays 154 and 156. A pull wire 158 extends through a lumen 160 of shaft 152 and through protrusions on each of the stays 154 and 156. A guide wire GW is received through the shaft 152 in order to permit vascular introduction by conventional techniques. The radially compressible prosthesis P (such as graft 10) is placed over the distal end of the shaft extension 162, generally being aligned between the stays 154 and 156. The pull wire 158 is then advanced through the stays 154 and 156 so that it passes through each end of the prosthesis P to maintain the prosthesis P in place until the pull wire is withdrawn. While the pull wire 158 remains in place, a prosthesis-containment sheath 164 may be axially advanced over the graft to radially compress the graft into its desired low profile diameter. The sheath 164 includes a flared (i.e., outwardly tapered) distal end 166 to facilitate advancing the sheath over the prosthesis P, in particular so that the prosthesis P may be recaptured when it is partially deployed. The outward flare may be permanently fixed in the body of the sheath, but will preferably be selectively deployable between the flared and non-flared configuration, using any of the mechanisms described above.

Figure 18A:
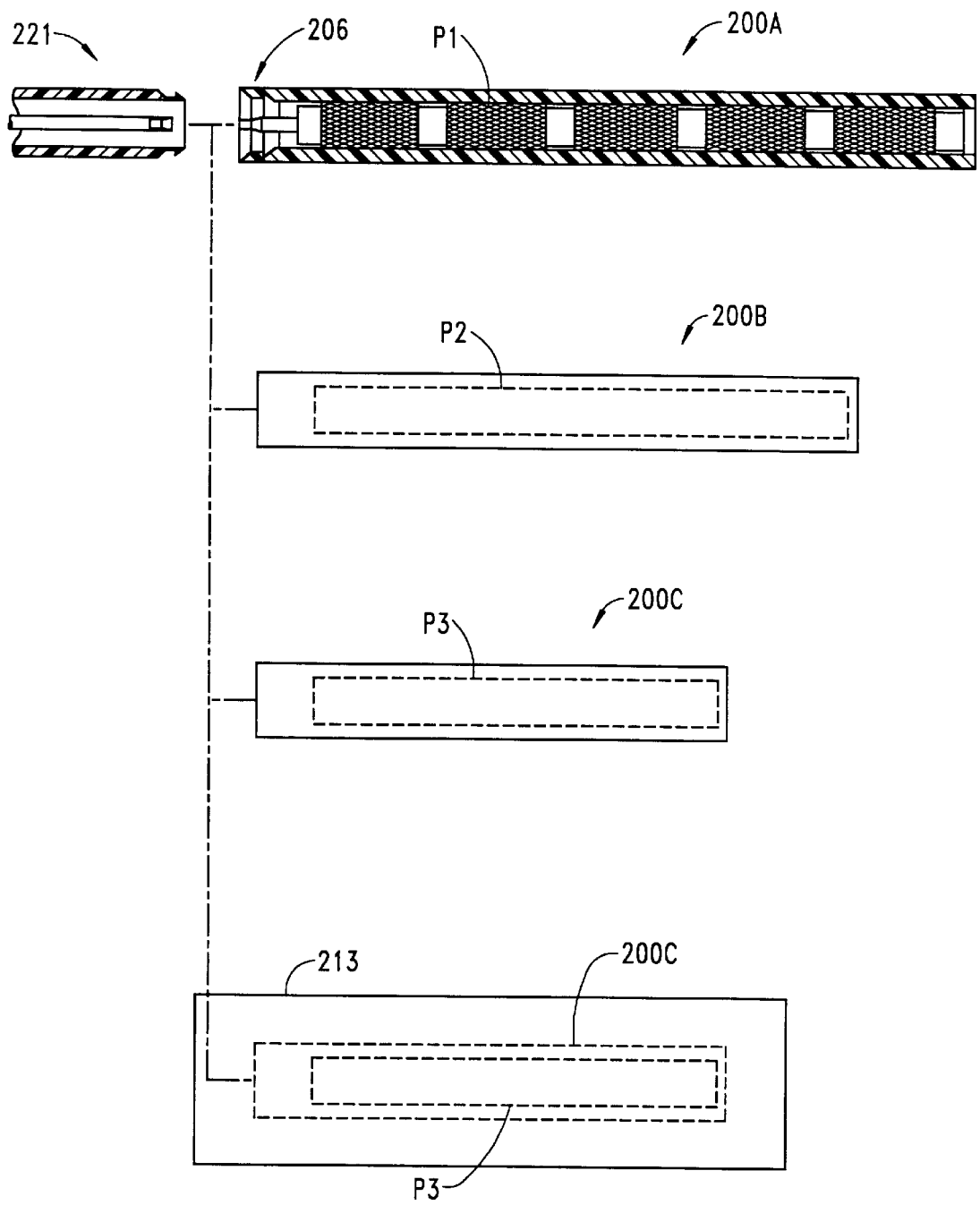
FIG. 18A illustrates a set of the prosthesis cartridges of FIGS. 17 and 18.

Referring now to FIGS. 17, 18, and 18A a prosthesis cartridge 200 comprises a sheath extension 202 having a distal end 204 and a proximal end 206. A prosthesis P is contained within the sheath extension 202 and is mounted over a shaft extension 208. Typically, the prosthesis P will be anchored on the shaft extension 208 using penetrating stays (not shown) as described in connection with previous embodiments. The prosthesis cartridge 200 is releasably connectable to a delivery catheter 221 including a sheath 220 (or other elongate member) and shaft 222. The proximal end of the cartridge sheath 202 is configured to couple to the distal end of the catheter sheath 220. Similarly, the proximal end of the shaft extension 208 is configured to selectively couple to the distal end of the shaft 222. "By providing prosthesis cartridges 200A, 200B, 200C, having a variety of useful lengths and or diameters, the need for maintaining a large inventory of delivery catheters can be greatly reduced." In this way, a user can select the diameter, length, and other characteristics of the prosthesis P1, P2, or P3 which are desired to be employed in a procedure. The prosthesis, which is part of cartridge 200 (and preferably packaged in a separate, sterile pouch 213 or other container) may then be attached to the distal end of the delivery catheter (which is separately packaged in a sterile pouch or other container) having the necessary sheath and shaft connections. The catheter sheath 220 could alternatively comprise other, non-tubular structures (elongate members). It is necessary only that the elongate member be able to connect to the sheath extension 202 to be proximally retracted over the prothesis P (and optionally distally advanced) to effect release and recapture of the prosthesis as described above.

Figure 19A:
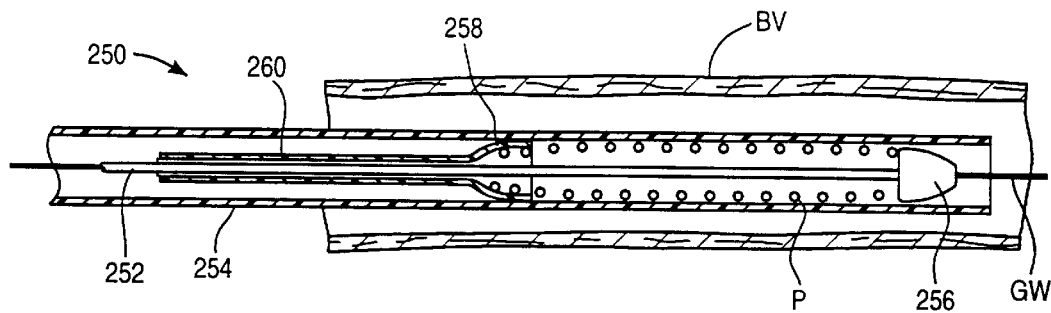
FIGS. 19A–19D illustrate a delivery catheter constructed in accordance with the principles of the present invention which includes a retaining structure comprising a pair of axially spaced-apart anchor members to hold the prosthesis in place as the sheath is drawn proximally from over the prosthesis.

Referring now to FIGS. 19A–19D, yet another embodiment of a delivery catheter 250 constructed in accordance with the principles of the present invention will be described. Delivery catheter 250 includes flexible shaft 252 having a central lumen for receiving a guide wire GW. A sheath 254 is slidably mounted over the shaft 252, generally as described for previous embodiments. The catheter 250 differs from previous embodiments, however, in the nature of the retaining structure which is used for holding prosthesis P in place on the flexible shaft 252. The retaining structure comprises a distal anchor 256, which is conveniently in the form of a cap or other receptacle which can receive a distal end of the prosthesis therein. A proximal anchor 258 is mounted at the distal end of a sliding tube 260. As shown in FIG. 19A, when the catheter 250 is introduced to blood vessel BV the prosthesis P will be maintained in its collapsed configuration by the anchors 256 and 258, and sheath 254 will cover the prothesis and anchor structures.

Figure 19B:
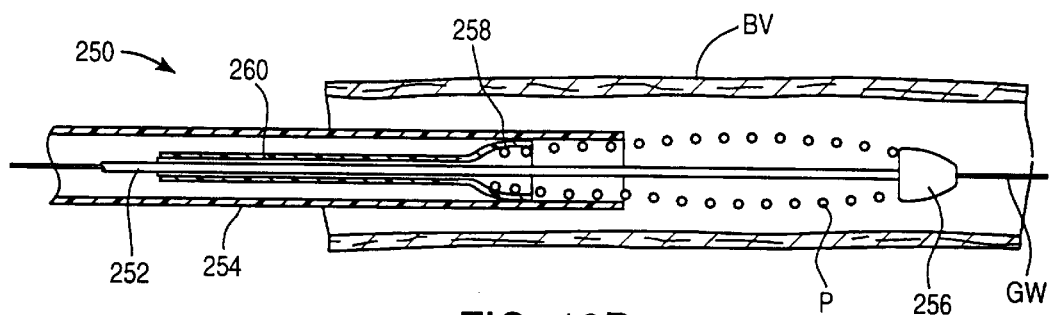
Figure 19C:
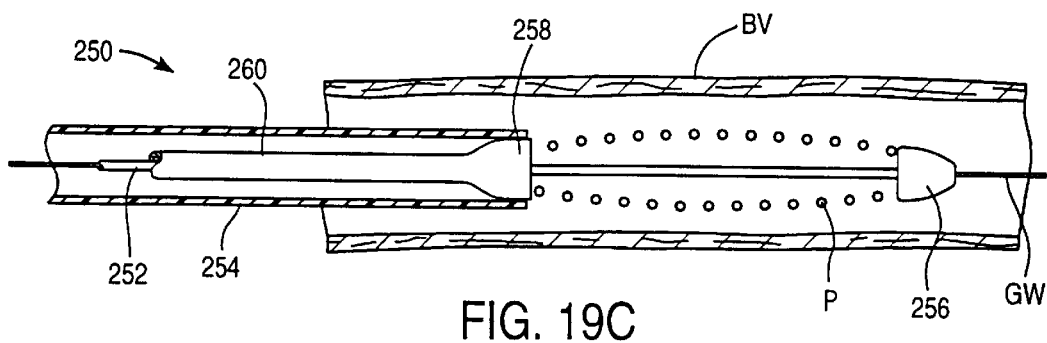
Figure 19D:
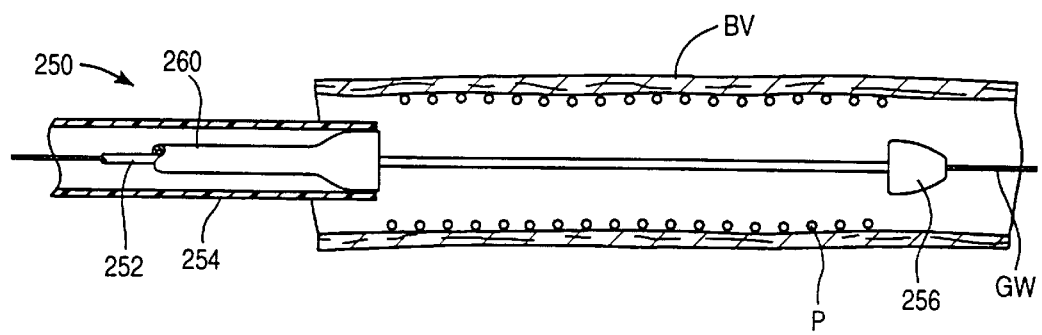

After introduction, as illustrated in FIG. 19B, the sheath 254 may be withdrawn proximally to expose the prosthesis P. The prosthesis P, however, remains radially compressed by the anchors 256 and 258, even after the sheath 254 has been fully withdrawn, as illustrated in FIG. 19C. The prosthesis P may be fully released by moving the anchors 256 and 218 axially apart in order to free the compressed ends of the prosthesis, as illustrated in FIG. 19D. Prior to release, however, the exposed prostheses can be carefully positioned without interference from the sheath 254. It is a particular advantage that such partial release is achieved while still being able to readily recapture the prosthesis by readvancing the sheath 254.

Figure 20A:
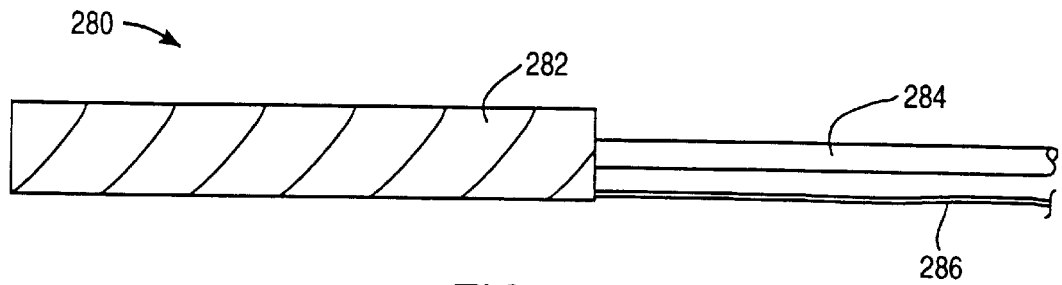
FIGS. 20A and 20B illustrate an alternative embodiment of a prosthesis cover structure according to the present invention, where the cover is a cylinder having a weakened line disposed helically over its surface. The cover may be opened by pulling proximally on one end of the cylinder.
Figure 20B:
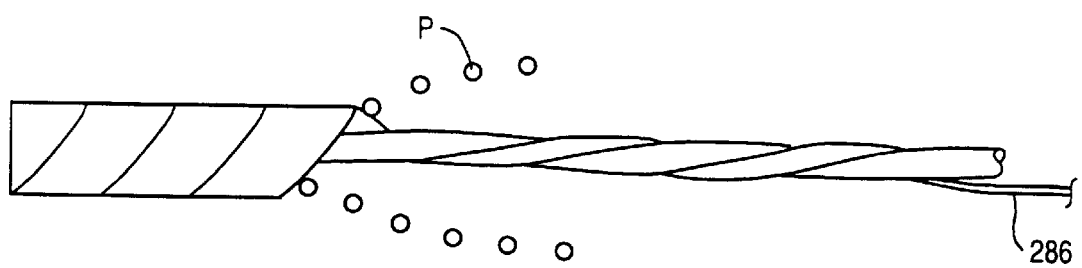

Referring now to FIGS. 20A and 20B, an alternative embodiment of a prostheses retaining structure is illustrated. The retaining structure 280 will fully cover and compress the prostheses P, and will usually be maintained within an outer sheath (not shown) equivalent to the delivery catheter sheaths illustrated previously. The retaining structure 280 will maintain radial compression of the prosthesis P within the sheath, regardless of whether the sheath covers the prosthesis. Thus, the sheath of the associated delivery catheter may be proximally retracted prior to release of the prostheses P.

The retaining structure 280 comprises a helically wound ribbon, which may optionally be formed as a helically scored or perforated cylinder. The retaining structure 280 is mounted on flexible shaft 284, typically with a distal portion of the helical ribbon attached directly or indirectly to the shaft. A pull cord 286 is attached to a proximal end of the helical ribbon, and the ribbon may be withdrawn from over the prostheses P by pulling proximally on the pull cord, as illustrated in FIG. 20b.

Figure 21A:
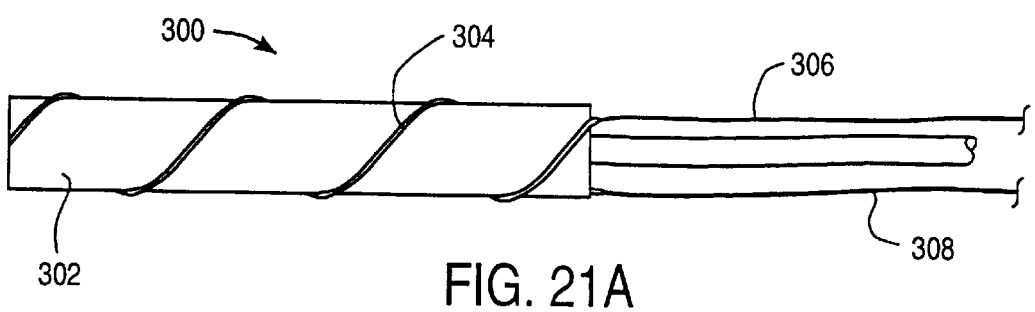
FIGS. 21A and 21B illustrate another alternative embodiment of the prosthesis cover structure of the present invention, where a tear wire is attached to a pull cord for opening the cover along a helical line.
Figure 21B:
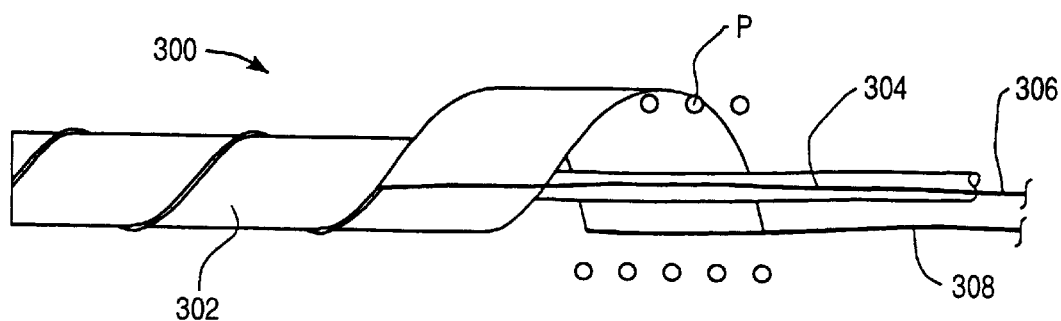

Yet another embodiment of the retaining structure of the present invention is illustrated in FIGS. 21A and 21B. Retaining structure 300 comprises a cylinder 302 having a helical wire 304 disposed over its surface. The wire 304, when pulled from the cylinder 302, separates adjacent sections of the cylinder so that they break apart, as illustrated in FIG. 21B. Thus, by attaching a first pull cord 306 to a proximal end of the wire 304, the wire can be withdrawn by pulling proximally. The resulting ribbon-like section of the cylinder may then be withdrawn by pulling on a second pull cord 308, also as shown in FIG. 21B. The prostheses P is thus released from the catheter.

Figure 22A:
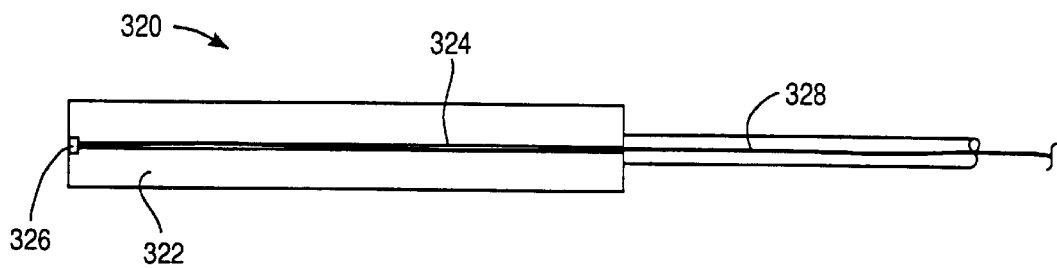
FIGS. 22A and 22B illustrate yet another embodiment of the prosthesis cover structure of the present invention, where a single axial line or perforation may be opened using a zipper structure.
Figure 22B:
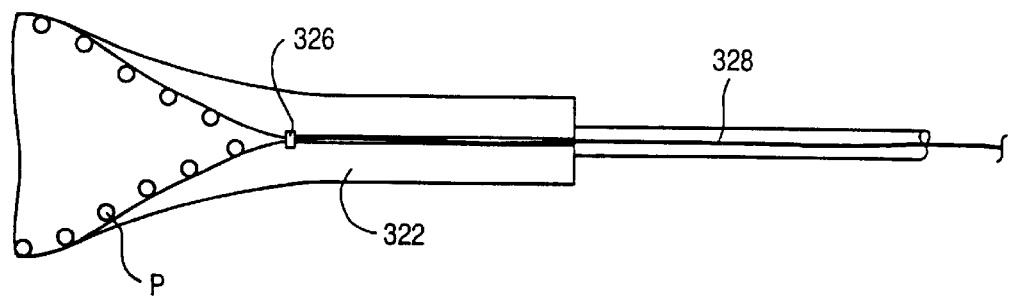

Yet another embodiment of a retaining structure of the present invention is illustrated in FIGS. 22A and 22B structure 320 is a cylinder 322 having a single axial break line 324 formed along one side thereof. It will be appreciated that more than one axial break line may be provided. Only one is illustrated, however, for convenience. A slide structure 326 secured to the cylinder 322 at a distal end of the break line 324. A pull cord 328 is attached to the slide structure 326. Optionally, multiple pull cords could be used. The slide structure 326 may be drawn proximally in order to open the breakline 324 in the manner of a zipper, as illustrated in FIG. 22B. In this way, the prostheses P can be released.

Figure 23A:
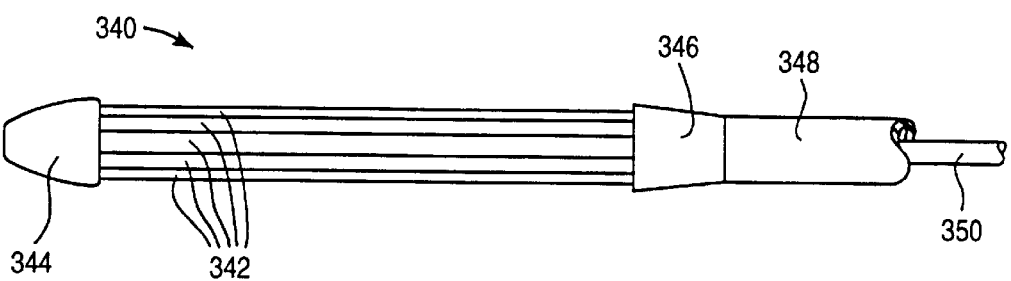
FIGS. 23A and 23B illustrate still another embodiment of the prosthesis cover structure of the present invention, where a plurality of radially flared resilient elements are held by an end cap and may be released by distally advancing the end cap.
Figure 23B:
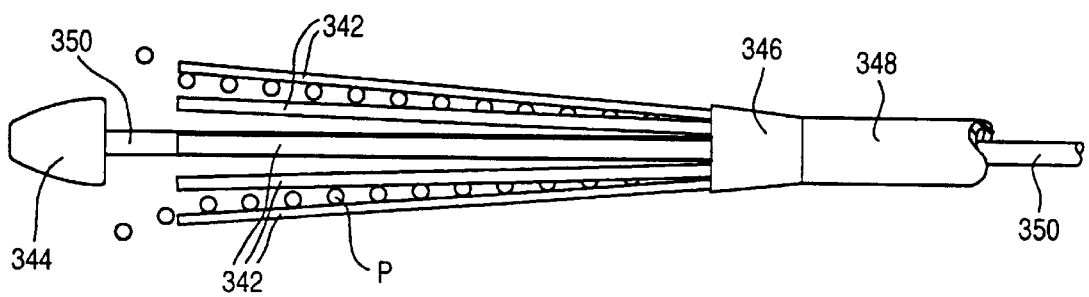

Yet another embodiment of the retaining structure 340 of the present invention is illustrated in FIGS. 23A and 23B. The retaining structure 340 comprises a plurality of individual resilient axial members 342 which are captured at their distal ends and an anchor 344. The axial elements 342 are permanently mounted in a ring structure 346 at the distal end of catheter body 348. The anchor 344 is secured at the distal end of a flexible shaft 350. The axial elements 342 are spring-loaded so that when the anchor 344 is moved distally by advancing the shaft 350, as illustrated in FIG. 23b, the individual elements will spring radially apart at the distal end. In this way, prosthesis P can be released from the retaining structure 340.

Figure 24A:
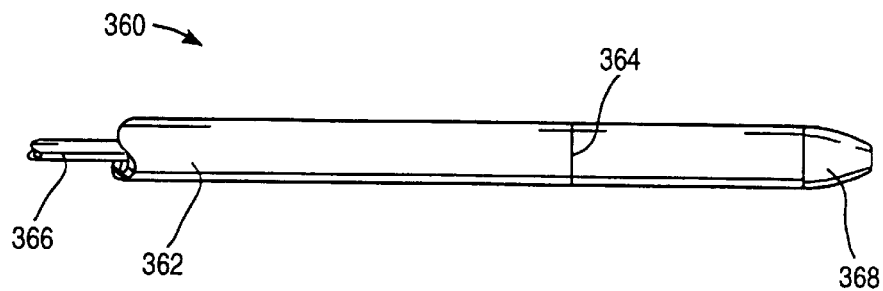
FIGS. 24A–24C illustrate yet another alternative embodiment of the prosthesis cover structure of the present invention, where the cover is weakened along a circumferential line, permitting the cover to be drawn axially apart to release the prosthesis.
Figure 24B:
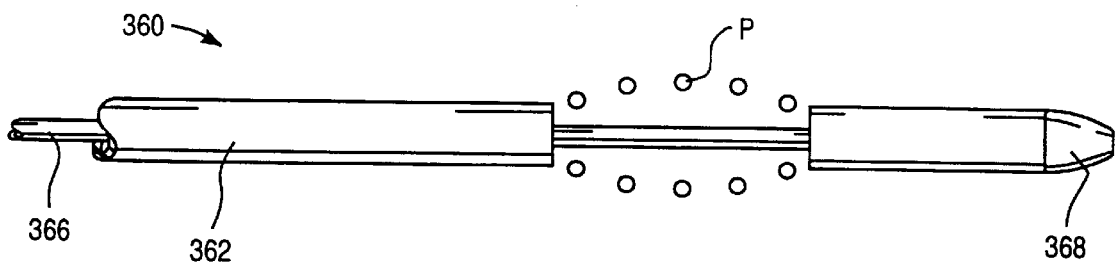
Figure 24C:
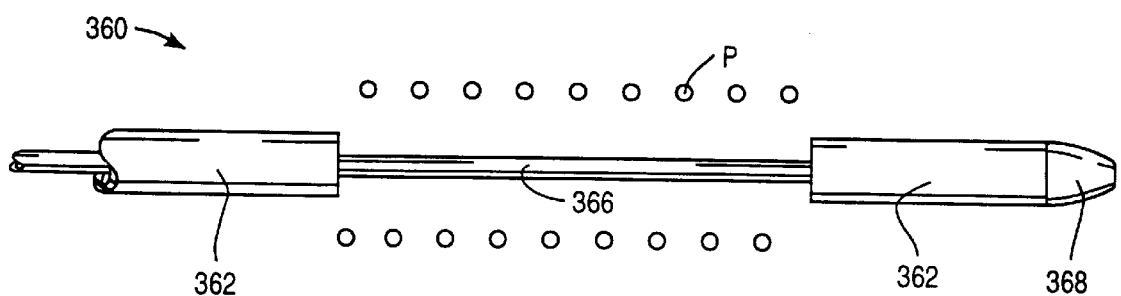

Referring now to FIGS. 24A–24C, still another embodiment of retaining structure constructed in accordance with the principles of the present invention will be described. The retaining structure 360 is a thin-walled tube 362 which is weakened along a circumferential (or helical) line 364, typically in the form of a score, perforation, or the like. Flexible shaft 366 secured to a distal end cap 368. By axially advancing the shaft 366, the end cap 368 and the attached portion of cylinder 362 between the score line 364 and the end cap will be pulled away from the remainder of the cylinder 362. In this way, the prostheses P can be released. The prostheses is first partially released, as shown in FIG. 24B. After the cylinder segments are fully spaced-apart, the prostheses is fully released, as shown in FIG. 24C.

Although the foregoing invention has been described in some detail by way of illustration and example, for purposes of clarity of understanding, it will be obvious that certain changes and modifications may be practiced within the scope of the appended claims.

What is claimed is:

1. A delivery catheter for positioning a resilient, tubular, radially compressible endoluminal prosthesis having a proximal end and a distal end, said catheter comprising:

an elongate flexible shaft having a proximal end and a distal end;

a retaining structure attached near the distal end of the shaft for releasably holding the axial position of the prosthesis on the shaft; and a sheath slidably received over the shaft to cover the prosthesis while said prosthesis is axially held on the shaft by the retaining structure;

wherein the retaining structure is disposable radially over an outer surface of the prosthesis and radially within an inner surface of the sheath, the retaining structure extending distally over the prosthesis from the proximal end of the prosthesis to the distal end of the prosthesis while the sheath covers the retaining structure.

2. A delivery catheter as in claim 1, wherein the shaft has a coupling mechanism spaced proximally of the distal end and the sheath has a coupling mechanism proximally of a distal end of the sheath, whereby a distal end of the catheter including the distal end of the shaft and the distal end of the sheath are detachable and alternative distal ends of the catheter may be attached.

3. A delivery catheter as claimed in claim 1, wherein the retaining structure comprises a plurality of resilient, radially outwardly flarable axial elements.

4. A delivery catheter for positioning a resilient, tubular, radially compressible endoluminal prosthesis having at least one radial aperture, said catheter comprising:

an elongate flexible shaft having a proximal end and a distal end;

a retaining structure attached near the distal end of the shaft for releasably holding the axial position of the prosthesis on the shaft; and a sheath slidably received over the shaft to cover the prosthesis while said prosthesis is axially held on the shaft by the retaining structure;

wherein the retaining structure comprises at least one locking stay extending radially from the shaft so as to extend through the aperture of the prosthesis and hold the prosthesis axially in place relative to the shaft as the sheath is axially translated relative to the shaft and a portion of the prosthesis expands resiliently.

5. A delivery catheter as in claim 4, wherein the locking stay is disposed over the shaft and extends radially outward by a distance sufficient to engage an interior surface of the sheath.

6. A delivery catheter as in claim 5, wherein the retaining structure comprises at least two circumferentially spaced-apart locking stays disposed over the shaft.

7. A delivery catheter for positioning a resilient, tubular, radially compressible endoluminal prosthesis having a proximal end and a distal end, said catheter comprising:

an elongate flexible shaft having a proximal end and a distal end;

a retaining structure attached near the distal end of the shaft for releasably holding the axial position of the prosthesis on the shaft; and a sheath slidably received over the shaft to cover the prosthesis while said prosthesis is axially held on the shaft by the retaining structure;

wherein the retaining structure is disposable between the prosthesis and the sheath so that the retaining structure extends axially over the prosthesis from its proximal end to its distal end while the sheath covers the retaining structure, the retaining structure comprising a cover which is detachably secured over the radially compressible prosthesis and means operable from the proximal end of the flexible shaft for detaching the cover from over the prosthesis to release said prosthesis.

8. A delivery catheter as in claim 7, wherein the cover is a cylinder and the detaching means is a mechanism selected from the group consisting of (a) a cord for splitting the cylinder along at least one axial or spiral line by drawing proximally on the cord, (b) an axially translatable end cap which captures a plurality of resilient, radially outwardly flared axial elements of the cylinder, and (c) means for axially separating two halves of the cylindrical cover.

9. A catheter system comprising:

a resilient, radially compressible endoluminal prosthesis having a proximal end and a distal end;

an elongate flexible shaft having a proximal end and a distal end;

a retaining structure attached near the distal end of the shaft which releasably holds the axial position of the prosthesis on the shaft; and a sheath slidably received over the shaft to cover the prosthesis while said prosthesis is axially held on the shaft by the retaining structure;

wherein the retaining structure extends distally over the prosthesis and within the sheath from a proximal end of the prosthesis beyond the distal end of the prosthesis while the sheath covers the retaining structure.

10. A catheter system as in claim 9, wherein the prosthesis is axially anchored by the retaining structure and is radially compressed by the sheath.

11. A catheter system as in claim 9, wherein the prosthesis is axially anchored and radially compressed by the retaining structure.

12. A delivery catheter as claimed in claim 9, wherein the cover comprises a plurality of resilient, radially outwardly flarable axial elements.

13. A delivery catheter for use with a prosthesis cartridge including a shaft extension having a distal end and a proximal end, a sheath extension slidably received over the shaft extension, the sheath extension having a distal end and a proximal end, and a prosthesis radially compressed over the shaft extension and within the sheath extension, said delivery catheter comprising:

an elongate flexible shaft having a proximal end, a distal end, and a coupling member at the distal end for coupling to the proximal end of the shaft extension of the prosthesis cartridge; and an elongate member slidably attached to the shaft and having a proximal end, a distal end, and a coupling member at the distal end for coupling to the proximal end of the sheath extension of the prosthesis cartridge so that the compressed prosthesis can be stored separately from the delivery catheter.

14. A delivery system comprising:

a resilient, radially compressible endoluminal prosthesis;

an elongate flexible shaft having a proximal end and a distal end;

a sheath slidably received over the shaft and prosthesis to radially restrain the prosthesis; and a plurality of resilient, radially outwardly flarable axial elements attached near the distal end of the shaft and extending distally over the prosthesis and within the sheath, resilient expansion of the prosthesis against the axial elements releasably holds the axial position of the entire prosthesis relative the shaft when the sheath slides relative to the axial elements.

* * * * *